United States Patent [19]

Matsumoto et al.

[11] Patent Number: 4,497,816
[45] Date of Patent: Feb. 5, 1985

[54] 7-(4-PYRIDYL)-1,8-NAPHTHYRIDINE DERIVATIVES AND THEIR ANTIBACTERIAL COMPOSITIONS

[75] Inventors: Jun-ichi Matsumoto, Ikoma; Yoshiro Nishimura, Suita; Shinichi Nakamura, Takatsuki, all of Japan

[73] Assignees: Dainippon Pharmaceutical Co., Ltd., Osaka, Japan; Laboratorie Roger Bellon, Neuilly sur Seine, France

[21] Appl. No.: 519,513

[22] Filed: Aug. 1, 1983

[30] Foreign Application Priority Data

Jul. 30, 1982 [JP] Japan .................. 57-134205

[51] Int. Cl.³ .................. A61K 31/435; C07D 471/04
[52] U.S. Cl. .................. 514/300; 546/126
[58] Field of Search .................. 546/123; 424/256

[56] References Cited

U.S. PATENT DOCUMENTS 4,341,784  7/1982  Matsumoto et al. .................. 424/256
4,359,578  11/1982 Matsumoto et al. .................. 544/362
4,382,937  5/1983  Matsumoto et al. .................. 424/256

FOREIGN PATENT DOCUMENTS 49355   4/1982  European Pat. Off. .
106681  7/1983  Japan .
1322318 7/1973  United Kingdom .

Primary Examiner—Henry R. Jiles
Assistant Examiner—Bernard I. Dentz
Attorney, Agent, or Firm—Wenderoth, Lind & Ponack

[57] ABSTRACT

A 7-(4-pyridyl)-1,8-naphthyridine compound of the formula

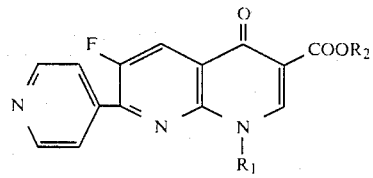

wherein $R_1$ is a hydrogen atom, an ethyl or vinyl group, and $R_2$ is a hydrogen atom or a lower alkyl group having 1 to 6 carbon atoms, and a salt thereof.

The compounds represented by the formula are useful in antibacterial compositions or intermediates thereof.

5 Claims, No Drawings

7-(4-PYRIDYL)-1,8-NAPHTHYRIDINE DERIVATIVES AND THEIR ANTIBACTERIAL COMPOSITIONS

The present invention relates to novel 7-(4-pyridyl)-1,8-naphthyridine derivatives having high antibacterial activities, their intermediates, and also antibacterial compositions containing the compounds as an active ingredient.

The present invention provides compounds of the following formula

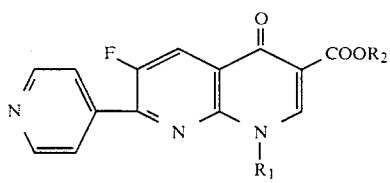

wherein $R_1$ is a hydrogen atom, an ethyl or vinyl group, and $R_2$ is a hydrogen atom or a lower alkyl group having 1 to 6 carbon atoms,
and salts thereof.

The compounds of formula (I) can also exist as a hydrate. Accordingly, the present invention includes hydrates of the compounds represented by formula (I).

The salts of the compounds (I) denote salts formed between the compound (I) and an acid or a base. Examples of the acid are inorganic acids such as hydrochloric acid, sulfuric acid; organic acids such as acetic acid, lactic acid, succinic acid, lactobionic acid, gultamic acid, aspartic acid and methanesulfonic acid. Examples of the base are sodium hydroxide, potassium hydroxide, sodium carbonate and potassium carbonate.

Among compounds of formula (I) of the present invention, compounds of the following formula

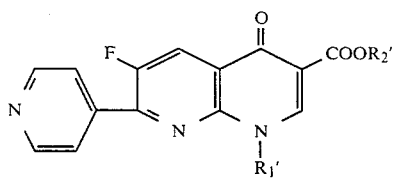

wherein $R_1'$ is a hydrogen atom, an ethyl or vinyl group, and $R_2'$ is a hydrogen atom or a lower alkyl group having 1 to 6 carbon atoms, excepting the case where $R_1'$ is an ethyl or vinyl group and $R_2'$ is a hydrogen atom,
are useful as intermediates for the synthesis of compounds of the following formula (I-B) which are dominated by the aforesaid formula (I),

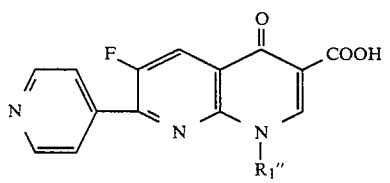

wherein $R_1''$ is an ethyl or vinyl group.

The compounds (I-B) and non-toxic pharmaceutically acceptable salts thereof exhibit superior antibacterial activity against Gram-positive bacteria such as Staphylococcus aureus, Gram-negative bacteria such as Escherichia coli and glucose-non-fermenters including Pseudomonas aeruginosa. Especially, Compound 1 mentioned below or its non-toxic pharmaceutically acceptable salt is most desirable as an antibacterial agent.

COMPOUND 1

1-Ethyl-6-fluoro-1,4-dihydro-4-oxo-7-(4-pyridyl)-1,8-naphthyridine-3-carboxylic acid

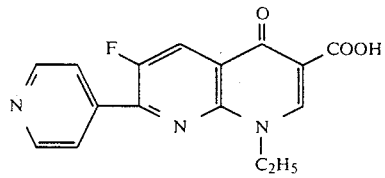

The structural characteristic of the compounds (I) of this invention consists in a combination of the substituents at the 6- and 7-positions of the 1,8-naphthyridine skeleton, and the compounds of formula (I) have a fluorine atom as the substituent at the 6-position and a 4-pyridyl group as the substituent at the 7-position.

The present inventors believe the following Compound A disclosed in British Pat. No. 1,322,318 to be structurally closest to the compounds of this invention.

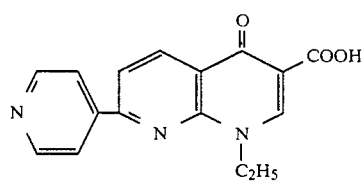

Compound A

British Pat. No. 1,322,318, however, does not describe or suggest a compound having a substituent at the 6-position, and as shown in Table 1 given hereinafter, the antibacterial activity of the compounds of this invention, particularly that in vivo, is far superior to that of compound A.

The compounds of the present invention are prepared by cyclizing a compound of the formula

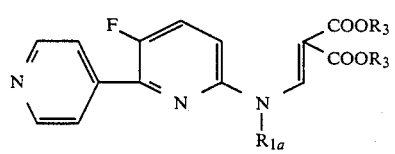

wherein $R_{1a}$ is a hydrogen atom, an ethyl or 2-halogenoethyl group, and $R_3$ is a lower alkyl group having 1 to 6 carbon atoms,
to form a compound of the formula

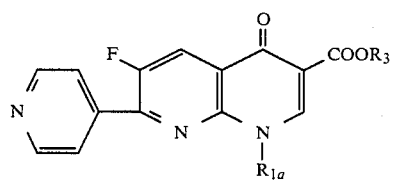

wherein $R_{1a}$ and $R_3$ are the same as defined above, and then, when the compound (b) in which $R_{1a}$ is a 2-halogenoethyl group is obtained, heating the compound to form a compound (I) in which $R_1$ is a vinyl group, and if desired, when the ester is obtained, hydrolyzing the ester to form a free carboxylic acid and if desired, when the compound (b) in which $R_{1a}$ is a hydrogen atom is obtained, ethylating the compound to form a compound (I) in which $R_1$ is an ethyl group, and optionally converting the compound of the formula (I) to its salt.

The cyclization reaction is performed by heating the compound (a) directly or in a high-boiling solvent such as diphenyl ether, diphenyl, o-dichlorobenzene, diphenylene oxide, dibutyl phthalate, or mixtures of these. The suitable heating temperature is 140° C. to 260° C. The cyclization reaction can also be performed in the presence of a conventional cyclization reagent such as polyphosphoric acid, an lower alkyl polyphosphate, concentrated sulfuric acid or phosphorus pentoxide. Where polyphosphoric acid or a lower alkyl polyphosphate is used, the reaction is carried out generally without an additional solvent. Where phosphorus pentoxide is used, the reaction carried out generally in a solvent such as benzene, dioxane or dimethylformamide. When concentrated sulfuric acid is used, the reaction is carried out generally in a solvent such as acetic anhydride or acetic acid. Depending upon the properties of the cyclization reagent, of course, it may serve also as the solvent. If the cyclization reagent is used, the reaction is carried out at relatively low temperature e.g., at a temperature of 100° C. to 160° C.

The heating process subsequent to the cyclization reaction is carried out in order to convert the 2-halogenoethyl moiety into a vinyl moiety. This reaction (vinylation reaction) is performed by heating the compound (b) in which $R_{1a}$ is a 2-halogenoethyl group, preferably in the presence of a catalyst. The catalysts used in the vinylation reaction are a metal hydroxide, a metal carbonate, a metal hydride such as sodium hydride, an alkali metal alkoxide such as sodium ethoxide, sodium methoxide or potassium butoxide, butyl lithium, pyridine, collidine or benzyltrimethylammonium hydroxide. The reaction temperature is selected from 50° to 270° C. The reaction may be carried out in the presence or absence of solvent, preferably in the presence of a solvent such as water, ethanol, acetic acid, dimethylformamide, dimethyl sulfoxide, ether, benzene, dioxane, tetrahydrofuran or pyridine.

Among compounds of the formula (I), the compounds of the formula (I-A) can be converted to other compounds of the formula (I) by the following process:
(1) ethylation process, or
(2) saponification process.

The ethylation process is generally carried out by reacting a compound (I-A) in which $R_1'$ is a hydrogen atom with an ethylating reagent. Examples of the ethylating reagent are ethyl halides such as ethyl iodide; and ethyl esters such as diethyl sulfate, ethyl p-toluenesulfonate or triethyl phosphate. The ethylation reaction is conducted by a conventional method, for example, by reacting a compound (I-A) in which $R_1'$ is hydrogen atom with an ethylating reagent in an inert solvent under heating. The inert solvent may be either an aqueous or non-aqueous solvent such as ethanol, dioxane, dimethylformamide, dimethyl sulfoxide or water. The reaction is accelerated by adding an acid-acceptor such as an alkali carbonate, and alkali hydroxide, an alkali metal alkoxide, sodium hydride, triethylamine or benzyltrimethylammonium hydride.

The saponification process is performed by hydrolyzing a compounds (I-A) in which $R_2'$ is a lower alkyl group having 1 to 6 carbon atoms to form the desired compound (I) in which $R_2$ is a hydrogen atom. This reaction is carried out by contacting the ester compound with water at 20° C. to 150° C. The hydrolysis is carried out generally in the presence of an acid or a base in order to accelerate the reaction. Specific examples of the acid are inorganic acids such as hydrochloric acid, hydrobromic acid, hydriodic acid, sulfuric acid or phosphoric acid; and organic acids such as acetic acid, oxalic acid or toluenesulfonic acid. Specific examples of the base are hydroxides such as sodium hydroxide or barium hydroxide; carbonates such as sodium carbonate or potassium carbonate; and sodium acetate.

The compounds (I) in which $R_1$ is a vinyl group are also prepared by the following process.

The compound (I-A) wherein $R_1'$ is a hydrogen atom is reacted with a compound of the formula

halogen—$CH_2CH_2$—Z  (c)

wherein Z is a halogen atom, a lower alkoxy group, a benzyloxy group, a hydroxyl group or its derivative, or a tertiary or quaternary amino group,
to form a compound of the formula

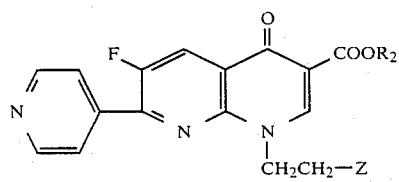

(d)

wherein $R_2$ and Z are the same as defined above,
and then heating the compound (d) to form the desired compound (I) in which $R_1$ is a vinyl group. The reaction between the compound (I-A) and the compound (c) can be performed in the same way as described above with regard to the ethylation process. Heating of the compound (d) is performed preferably in the presence of a catalyst. The catalysts used in the heating reaction are the common acids such as hydrochloric acid, sulfuric acid, polyphosphoric acid, phosphoric anhydride, formic acid, acetic acid, toluenesulfonic acid or potassium hydrogen sulfate, Lewis acids such as thionyl chloride, phosphorous oxychloride, boron trifluoride or zinc chloride; alkali hydroxides, alkali carbonates, metal hydrides such as sodium hydride, alkali metal alkoxides such as sodium ethoxide, sodium methoxide or potassium butoxide, pyridine, collidine, benzyltrimethylammonium hydroxide, acetic anhydride, phthalic anhydride, silver oxide, iodine, or butyl lithium. The reaction temperature is from 50° to 270° C. The reaction may be carried out in the presence or absence of solvent, preferably in the presence of a solvent such as water, ethanol, acetic acid, dimethylformamide, dimethyl sulfoxide, ether, benzene, dioxane, tetrahydrofuran, pyridine or a mixture thereof. Specific examples of the hydroxyl derivative as Z are acyloxy groups such as acetyloxy, benzoyloxy, ethoxycarbonyloxy, arylsulfonyloxy, lower alkylsulfonyloxy, S-aryl dithiocarbonyloxy or S-lower alkyl dithiocarbonyloxy. Specific examples of the tertiary or quaternary amino group as Z are $—N(CH_3)_2$, $—N(C_2H_5)_2$,

$-N^{\oplus}(CH_3)_3\ I^{\ominus}$, $-N^{\oplus}(C_2H_5)_3OH^{\ominus}$ or

The compounds of the present invention prepared by the above mentioned processes can be isolated and purified by usual methods. In the isolation and/or purification the compounds may be converted into the form of a salt, free carboxylic acid or free amine, depending on the conditions of isolation and/or purification.

The compounds of the present invention may be converted to each other in the desired form by usual methods.

The starting compounds (a) mentioned above are novel. The compounds (a) are prepared in accordance with the method described in Reference Example 1 given hereinafter.

The novel compounds (I-B) of the present invention, as will be shown in Table 1 given hereinbelow, have excellent antibacterial activities and low toxicity. Accordingly, the compounds (I-B) of the invention, especially Compound 1 and its non-toxic pharmaceutically acceptable salt can be used for the treatment or prevention of bacterial infections of warm-blooded animals including man.

Antibacterial activities of the Compound 1 of the present invention are illustrated in the following Table 1.

TABLE 1

|  | Item | Compound 1 | A[*1] | NA[*2] |
|---|---|---|---|---|
| [*3]In vitro antibacterial activity (MIC: μg/ml) | Staphylococcus aureus No. 50774 | 0.2 | 1.56 | 50 |
|  | Escherichia coli P-5101 | 0.2 | 0.78 | 3.13 |
|  | Psuedomonas aeruginosa No. 12 | 3.13 | 12.5 | 200 |
| [*4]In vivo efficacy against the systemic infections in mice (ED$_{50}$: mg/kg) | Staphylococcus aureus No. 50774 | 2.84 | 23.7 | 767 |
|  | Escherichia coli P-5101 | 3.1 | 21.0 | 29.2 |
|  | Pseudomonas aeruginosa No. 12 | 12.2 | >100 | 267 |
| [*5]Acute toxicity in mice (LD$_{50}$: mg/kg) |  | >2,000 | — | — |

Note:
[*1]Compound A: 1-ethyl-1,4-dihydro-4-oxo-7-(4-pyridyl)-1,8-naphthyridine-3-carboxylic acid (British Patent 1,322,318)
[*2]NA (nalidixic acid): 1-ethyl-1,4-dihydro-7-methyl-4-oxo-1,8-naphthyridine-3-carboxylic acid (U.S. Pat. No. 3,149,104)
[*3]In vitro antibacterial activity
The minimum inhibitory concentrations (MIC: μg/ml) shown in Table 1 were determined according to the agar dilution method recommended by Japan Society of Chemotherpy (1980)
[*4]In vivo efficacy
Compounds 1, A and NA were each suspended in a 0.2% aqueous solution of sodium carboxymethylcellulose. Each of the solutions was orally administered to mice infected with each of the test organisms under the conditions described below, and the median TABLE 1-continued

|  | Compound | | |
|---|---|---|---|
| Item | 1 | A[*1] | NA[*2] | effective dose (ED$_{50}$) was calculated in accordance with the Behrens-Kaerber method [Arch. Exp. Path. Pharm. 162 480 (1931)].
Experimental conditions:
Mice: Male mice (ddY) weighing about 20 g
Infection:
Staphylococcus aureus No. 50774
Intravenous infection with about $5 \times 10^8$ cells per mouse suspended in saline
Escherichia coli P-5101
Intraperitoneal infection with about $9 \times 10^6$ cells per mouse suspended in trypto-soy broth with 4% mucin
Pseudomonas aeruginosa No. 12
Intraperitoneal infection with about $5 \times 10^3$ cells per mouse suspended in trypto-soy broth with 4% mucin
Medication:
Twice, about 5 minutes and 6 hours after infection
Observation:
Staphylococcus aureus No. 50774-for 14 days Escherichia coli P-5101
Pseudomonas aeruginosa No. 12 } for 7 days

[*5]Acute oral toxicity in mice
A suspension containing compound 1 in various concentrations was orally given to female mice (ddY) at a volume of 0.1 ml per 10 g of body weight. The number of dead mice was counted after 7 days, and the value of median lethal dose (LD$_{50}$) was calculated in accordance with the Behrens-Kaerber method.

The dose of the compounds (I-B) of this invention may vary with the age, body weight and conditions of the subjects, the administration route, the number of administrations or the like, but is in the range of 0.3 to 80 mg per kilogram of body weight per day, preferably 1.3 to 50 mg per kilogram of body weight per day, for administration to man. The dose may be divided and administered two to several times per day. The administration route may be oral or parenteral, preferably oral or topical.

The compounds (I-B) of the present invention can be administered alone, but usually is administered in the form of a pharmaceutical preparation with pharmaceutically acceptable carriers or adjuvants. Specific examples of the pharmaceutical preparation are tablets, capsules, granules, fine granules, powders, syrups, etc. These pharmaceutical preparations are prepared in accordance with the customary manner. The adjuvants and carriers are those which are usually used in the field of pharmaceutical preparation and do not react with the compounds of the present invention, such as starch, mannitol, crystalline celulose, sodium carboxymethylcellulose, or the like.

They may further contain other therapeutically valuable substances according to the purpose of medication.

The pharmaceutical preparation of this invention, for examples tablets and capsules, may contain about 10 to about 700 mg, generally 50 to 500 mg of the compound (I-B) of this invention, per tablet or capsule. These amounts are not critical, and may be varied according to whether the required amount of the compound (I-B) of this invention is administered at a time or dividedly.

The compounds (I-B) of this invention may also be used as medicine for fish diseases, agricultural chemicals or food preservatives.

The processes for producing the novel compounds of the invention are illustrated below.

Reference Example 1 shows a process for the preparation of the starting compound.

Examples 1 and 2 illustrate processes for the preparation of the compounds of this invention.

Examples 3 and 4 show the preparation of pharmaceuticals containing the Compound 1 of this invention.

REFERENCE EXAMPLE 1

Process for preparation of the starting compound:

1,2-Dihydro-2-oxo-6-(4-pyridyl)pyridine-3-carbonitrile (47 g), which was disclosed in British Pat. No. 1,322,318, was nitrated with a mixture of concentrated sulfuric acid and fuming nitric acid to give 1,2-dihydro-5-nitro-2-oxo-6-(4-pyridyl)nicotinic acid (35 g, m.p. above 300° C.), which was decarboxylated by heating in 80% sulfuric acid, followed by chlorination with phosphorous oxychloride to yield 2-chloro-5-nitro-6-(4-pyridyl)pyridine (18.8 g, m.p. 137°–138° C.). This compound was treated with ammonia in ethanol, and treated with acetic anhydride to give 2-acetylamino-5-nitro-6-(4-pyridyl)pyridine (16.9 g), which was subjected to catalytic hydrogenation with Raney nickel. The catalyst was filtered off, and the filtrate was concentrated to dryness. To the residue were added 42% tetrafluoroboric acid and sodium nitrite. The corresponding diazonium compound was formed. The diazonium compound was heated in xylene to give 2-acetylamino-5-fluoro-6-(4-pyridyl)pyridine (9.1 g, m.p. 254°–256° C.), which was hydrolyzed with hydrochloric acid to yield 6-amino-3-fluoro-2-(4-pyridyl)pyridine (7.3 g, m.p. 189°–190° C.). This compound was condensed with diethyl ethoxymethylenemalonate to give diethyl N-[3-fluoro-2-(4-pyridyl)-6-pyridyl]amino-methylenemalonate (11.5 g, m.p. 140°–141°).

EXAMPLE 1

Process for preparation of Compound 1:

A suspension of diethyl N-[3-fluoro-2-(4-pyridyl)-6-pyridyl]aminomethylenemalonate (11.5 g) in 120 ml of Dowtherm A was heated to reflux for 10 minutes and then cooled to room temperature. The resulting solid was filtered off. The filtrate was heated to reflux for 10 minutes and the solid was collected. The combined solid was washed successively with ethanol and ether to give ethyl 6-fluoro-1,4-dihydro-4-oxo-7-(4-pyridyl)-1,8-naphthyridine-3-carboxylate (7.2 g, m.p. 280°–285° C.).

A mixture containing 2.63 g of ethyl 6-fluoro-1,4-dihydro-4-oxo-7-(4-pyridyl)-1,8-naphthyridine-3-carboxylate, 0.42 g of 50% sodium hydride (dispersed in mineral oil) and 30 ml of dimethylformamide was heated at 50°–60° C. for 10 minutes. To the stirred mixture was added 1.31 g of ethyl iodide, and heating was continued for 1.5 hours. The reaction mixture was filtered and the filtrate was concentrated to dryness in vacuo and the residue was taken up in a mixture of chloroform and water. The chloroform layer was separated and the chloroform was evaporated in vacuo to give crystals which were recrystallized from ethyl acetate to yield ethyl 1-ethyl-6-fluoro-1,4-dihydro-4-oxo-7-(4-pyridyl)-1,8-naphthyridine-3-carboxylate (2.1 g, m.p. 185°–186° C.). This compound was heated at 90°–100° C. with 25 ml of 2N sodium hydroxide for 5 minutes. The reaction mixture was treated with decolorizing charcoal and filtered. The filtrate was adjusted to pH 6–7 with acetic acid and chilled. The resulting solid was collected by filtration and recrystallized from ethanol to give 1-ethyl-6-fluoro-1,4-dihydro-4-oxo-7-(4-pyridyl)-1,8-naphthyridine-3-carboxylic acid (Compound 1) (1.5 g, m.p. 286°–288° C.).

EXAMPLE 2

Process for preparation of Compound 2:

Ethyl 6-fluoro-1,4-dihydro-4-oxo-7-(4-pyridyl)-1,8-naphthyridine-3-carboxylate (4.0 g), which was prepared by the method of the above Example 1, was suspended in 40 ml of dimethylformamide. To the suspension was added 620 mg of 50% sodium hydride (dispersed in mineral oil) and the mixture was heated 50°–60° C. for 10 minutes. To the stirred mixture was added 1.6 g of ethylenebromohydrin. The mixture was heated for 1.5 hours and then filtered. The filtrate was concentrated to dryness in vacuo. The residue was taken up in a mixture of chloroform and water. The chloroform layer was separated and the chloroform was evaporated in vacuo to give crystals which were recrystallized from ethanol to give ethyl 6-fluoro-1,4-dihydro-1-(2-hydroxyethyl)-4-oxo-7-(4-pyridyl)-1,8-naphthyridine-3-carboxylate (3.0 g, m.p. 223°–225° C.). To a solution of this compound in 50 ml of chloroform was added 2.0 g of thionylchloride. The mixture was heated to reflux for 30 minutes, concentrated to dryness in vacuo, and then poured into ice-water. The solution was neutralized with 10% sodium hydroxide and extracted with chloroform. The chloroform was evaporated in vacuo and the residue was crystallized from acetonitrile to give ethyl 1-(2-chloroethyl)-6-fluoro-1,4-dihydro-4-oxo-7-(4-pyridyl)-1,8-naphthyridine-3-carboxylate (2.6 g, m.p. 192°–194° C.).

Ethyl 1-(2-chloroethyl)-6-fluoro-1,4-dihydro-4-oxo-7-(4-pyridyl)-1,8-naphthyridine-3-carboxylate was suspended in 1N sodium hydroxide and the suspension was heated at 70° C. for 4 hours. The precipitate was collected by filtration, and dissolved in water. Then the pH of the solution was adjusted to about 6 with acetic acid. The resulting solid was collected and recrystallized from ethanol to give 6-fluoro-1,4-dihydro-4-oxo-7-(4-pyridyl)-1-vinyl-1,8-naphthyridine-3-carboxylic acid (Compound 2) (0.22 g, m.p. 254°–257° C.).

EXAMPLE 3

| | |
|---|---|
| Compound 1 | 250 g |
| Starch | 50 g |
| Lactose | 35 g |
| Talc | 15 g |

The above components were blended and granulated and filled into 1,000 capsules in accordance with conventional methods.

EXAMPLE 4

| | |
|---|---|
| Compound 1 | 250 g |
| Starch | 54 g |
| Calcium carboxymethyl cellulose | 40 g |
| Micocrystalline cellulose | 50 g |
| Magnesium stearate | 6 g |

The above components were blended, granulated and made into tablets in a manner known per se. Thus, 1,000 tablets each weighing 400 mg were formed.

What we claim is:

1. A 7-(4-pyridyl)-1,8-naphthyridine compound of the formula

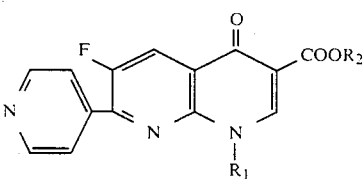

wherein $R_1$ is a hydrogen atom, an ethyl or vinyl group, and $R_2$ is a hydrogen atom or a lower alkyl group having 1 to 6 carbon atoms, or a salt thereof.

2. A 7-(4-pyridyl)-1,8-naphthyridine compound of the formula

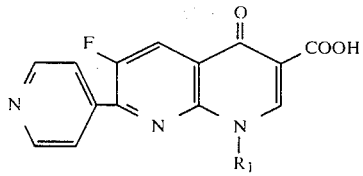

wherein $R_1$ is an ethyl or vinyl group, or a non-toxic pharmaceutically acceptable salt thereof.

3. 1-Ethyl-6-fluoro-1,4-dihydro-4-oxo-7-(4-pyridyl)-1,8-naphthyridine-3-carboxylic acid or a non-toxic pharmaceutically acceptable salt thereof.

4. 6-Fluoro-1,4-dihydro-4-oxo-7-(4-pyridyl)-1-vinyl-1,8-naphthyridine-3-carboxylic acid or a non-toxic pharmaceutically acceptable salt thereof.

5. A pharmaceutical composition comprising an antibacterially effective amount of a 7-(4-pyridyl)-1,8-naphthyridine compound of the formula

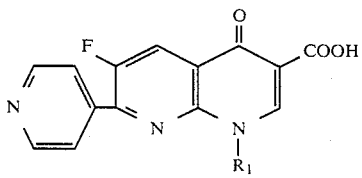

wherein $R_1$ is an ethyl or vinyl group, or a non-toxic pharmaceutically acceptable salt thereof, and a non-toxic pharmaceutically acceptable carrier therefor.

* * * * *

UNITED STATES PATENT AND TRADEMARK OFFICE
CERTIFICATE OF CORRECTION

PATENT NO. : 4,497,816

DATED : February 5, 1985

INVENTOR(S) : Jun-ichi MATSUMOTO; Yoshiro NISHIMURA; Shinichi NAKAMURA

It is certified that error appears in the above-identified patent and that said Letters Patent is hereby corrected as shown below:

On the cover page, the left column, under "[73] Assignees:" correct the spelling of "Laboratoire".

Column 3, line 68, change "and" to --an--.

Column 4, line 2, change "hydride" to --hydroxide--.

Column 5, correct TABLE 1 appearing at lines 38 to 54 to read as follows:

TABLE 1

| Item | | Compound 1 | A[*1] | NA[*2] |
|---|---|---|---|---|
| [*3]In vitro antibacterial activity (MIC: μg/ml) | *Staphylococcus aureus* No. 50774 | 0.2 | 1.56 | 50 |
| | *Escherichia coli* P-5101 | 0.2 | 0.78 | 3.13 |
| | *Psuedomonas aeruginosa* No. 12 | 3.13 | 12.5 | 200 |
| [*4]In vivo efficacy against the systemic infections in mice ($ED_{50}$: mg/kg) | *Staphylococcus aureus* No. 50774 | 2.84 | 23.7 | 767 |
| | *Escherichia coli* P-5101 | 3.1 | 21.0 | 29.2 |
| | *Pseudomonas aeruginosa* No. 12 | 12.2 | >100 | 267 |
| [*5]Acute toxicity in mice ($LD_{50}$: mg/kg) | | >2,000 | — | — |

UNITED STATES PATENT AND TRADEMARK OFFICE
CERTIFICATE OF CORRECTION

PATENT NO. : 4,497,816

DATED : February 5, 1985

INVENTOR(S) : Jun-ichi MATSUMOTO; Yoshiro NISHIMURA; Shinichi NAKAMURA

It is certified that error appears in the above-identified patent and that said Letters Patent is hereby corrected as shown below:

Column 6, delete lines 1 to 4 inclusive;

line 7, correct the line to read:

--Pharm. 162 480 (1931)]--.

Column 6, line 67, change "medicine" to --medicines--.

Signed and Sealed this

Thirteenth Day of August 1985

[SEAL]

Attest:

DONALD J. QUIGG

Attesting Officer

Acting Commissioner of Patents and Trademarks